US012650425B1

(12) United States Patent
Sadrzadeh et al.

(10) Patent No.: US 12,650,425 B1
(45) Date of Patent: Jun. 9, 2026

(54) METHODS AND SYSTEMS FOR NON-INVASIVELY ASSESSING VIABILITY IN HUMAN OOCYTES USING METABOLIC AND MORPHOLOGICAL MEASURES

(71) Applicant: Noor Sciences Inc., Los Altos, CA (US)

(72) Inventors: Naz Sadrzadeh, Los Altos, CA (US); Kaveh Azartash, Aliso Viejo, CA (US); Nader Sadrzadeh, Los Altos, CA (US)

(73) Assignee: Noor Sciences Inc., Los Altos, CA (US)

( * ) Notice: Subject to any disclaimer, the term of this patent is extended or adjusted under 35 U.S.C. 154(b) by 358 days.

(21) Appl. No.: 18/387,661

(22) Filed: Nov. 7, 2023

Related U.S. Application Data

(63) Continuation-in-part of application No. 18/371,906, filed on Sep. 22, 2023, now Pat. No. 12,536,658.

(60) Provisional application No. 63/423,902, filed on Nov. 9, 2022, provisional application No. 63/410,157, filed on Sep. 26, 2022.

(51) Int. Cl.
　　G01N 21/3563 (2014.01)
　　G01N 33/50 (2006.01)

(52) U.S. Cl.
　　CPC ..... G01N 33/5091 (2013.01); G01N 21/3563 (2013.01)

(58) Field of Classification Search
　　CPC ..................... G01N 33/5091; G01N 21/3563
　　See application file for complete search history.

(56) References Cited

U.S. PATENT DOCUMENTS

| | | | | |
|---|---|---|---|---|
| 9,984,278 | B2 * | 5/2018 | Needleman | ........ G01N 33/5091 |
| 2015/0268227 | A1 * | 9/2015 | Tan | ........................ G06T 7/0016 435/29 |
| 2015/0346100 | A1 * | 12/2015 | Racowsky | ......... G01N 21/6408 435/34 |
| 2017/0039415 | A1 * | 2/2017 | Needleman | .......... G06V 20/695 |
| 2018/0239950 | A1 * | 8/2018 | Needleman | ........... G06T 7/0012 |
| 2019/0113423 | A1 * | 4/2019 | Goodman | ................ G01N 1/36 |
| 2019/0376012 | A1 * | 12/2019 | Pedersen | ........... G01N 21/6408 |
| 2020/0320708 | A1 | 10/2020 | Ma et al. | |
| 2022/0328188 | A1 * | 10/2022 | Sanchez | ................ G16H 10/40 |

FOREIGN PATENT DOCUMENTS

KR 　　20150107774 A 　 * 　9/2015 　 ........ G01N 21/6408

OTHER PUBLICATIONS

Barberet et al., What impact does oocyte vitrification have on epigenetics and gene expression?, Clinical Epigenetics, vol. 12:121, 2020.

(Continued)

*Primary Examiner* — Tsung Yin Tsai
(74) *Attorney, Agent, or Firm* — Clause Eight; Michael Catania

(57) ABSTRACT

Methods and systems to assess the viability of human oocytes for egg vitrification or cryopreservation process are disclosed herein. The method utilizes fluorescence lifetime imaging microscopy (FLIM) coupled with integrating an oocyte's morphological endpoints, such as shape and size, to assess and identify the viability in human oocytes. The method and system also use data analysis software capable of correlating PH values, FLIM data, and chromosomal health assessments to determine the viability of human oocytes.

11 Claims, 14 Drawing Sheets

(56) References Cited

OTHER PUBLICATIONS

Bertoldo et al., NAD+ Repletion Rescues Female Fertility During Reproductive Aging, Cell Rep., vol. 30(6): pp. 1670-1681, Feb. 11, 2020.

Boldt et al., Human oocyte cryopreservation: 5-year experience with a sodium-depleted slow freezing method, Reproductive BioMedicine Online, vol. 13, No. 1, pp. 96-100, 2006.

Christou-Kent et al., Diversity of RNA-Binding Proteins Modulating Post-Transcriptional Regulation of Protein Expression in the Maturing Mammalian Oocyte, Cells, vol. 9, 662, Mar. 9, 2020.

Cobo et al., Comparison of concomitant outcome achieved with fresh and cryopreserved donor oocytes vitrified by the Cryotop method, Fertility and Sterility, vol. 89, No. 6, Jun. 2008.

Lee et al., Oocyte Maturity in relation to Woman's Age in In Vitro Fertilization Cycles Stimulated by Single Regimen, Yonsei Med Journal, vol. 53(1) 181-185, 2012.

Moghadam et al., Oocyte quality and aging, JBRA Assisted Reproduction, vol. 26(1), 105-122, 2022.

Venturas et al., Noninvasive metabolic profiling of cumulus cells, oocytes, and embryos via fluorescence lifetime imaging microscopy: a mini-review, Human Reproduction, vol. 38, No. 5, pp. 799-810, 2023.

Potdar et al., Oocyte vitrification in the 21st century and post-warming fertility outcomes: a systematic review and meta analysis, Reproductive Biomedicine Online vol. 29, 159-176, 2014.

Rienzi et al., Oocyte, embryo and blasctocyst cryopreservation in ART: systematic review and meta-analysis comparing slow-freezing versus vitrification to produce evidence for the development of global guidance, Human Reproduction Update, vol. 23, No. 2, pp. 139-155, 2017.

Rotllan et al., Therapeutic Potential of Emerging NAD+-Increasing Strategies for Cardiovascular Diseases, Antioxidants vol. 10, 1939, 2021.

Zegers-Hochschild et al., The International Glossary on Infertility and Fertility Care, 2017, Human Reproduction, vol. 32, No. 9, pp. 1786-1801, 2017.

* cited by examiner

200

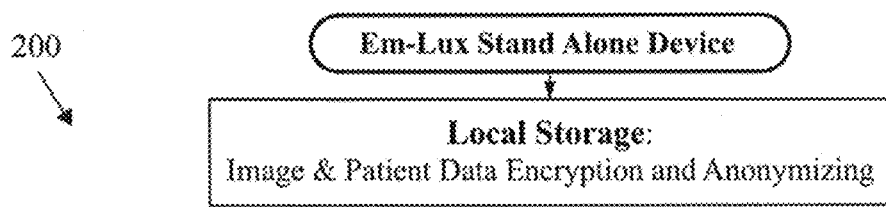

Assessing Metabolic Endpoints with FLIM

Photon lifetime decay data analyzed to create a 2D heatmap.

Decode novel phasor plot on good quality embryos for desired biological components (ICM, TE, ZP) through Gaussian Mixture Models.

Multiple 2D and 3D plots generated for distribution visualization for all Z-plane captured data on identified clusters.

Feature extraction of variables from phasor plot density contours.

Component analysis, PCA, and harmonic analysis to refine data classification.

Collecting Embryo PH

Collect PH from media.

Assign PH value a numerical value based on acidic or basic conditions.

Assessing Patient Demographic and Sibling Data

Collect, annonymize, and encrypt available data (age, medical Hx, current Rx)

Collect parental and sibling information (number of males vs. femailes, twins, etc.)

All Data from Pipelines are Collected and Used at the Final Classification Stage

Apply deep learning models, such as LSTM, and test different classification tasks, such as aneuploid vs. euploid.

Tag Embryos based on highest probabilities for positive class using tools, suxh as XGBoost, with their viabilities.

FIG. 2A

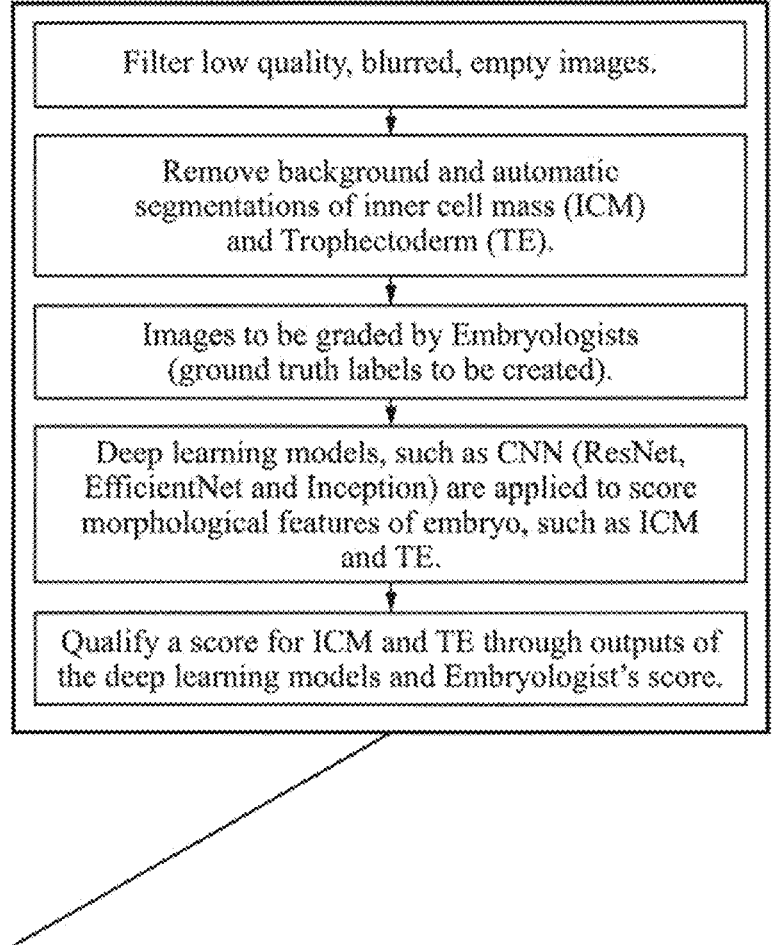

**Collecting and Analyzing Numberical Values
to Assess Morphology of ICM and TE**

Filter low quality, blurred, empty images.

Remove background and automatic
segmentations of inner cell mass (ICM)
and Trophectoderm (TE).

Images to be graded by Embryologists
(ground truth labels to be created).

Deep learning models, such as CNN (ResNet,
EfficientNet and Inception) are applied to score
morphological features of embryo, such as ICM
and TE.

Qualify a score for ICM and TE through outputs of
the deep learning models and Embryologist's score.

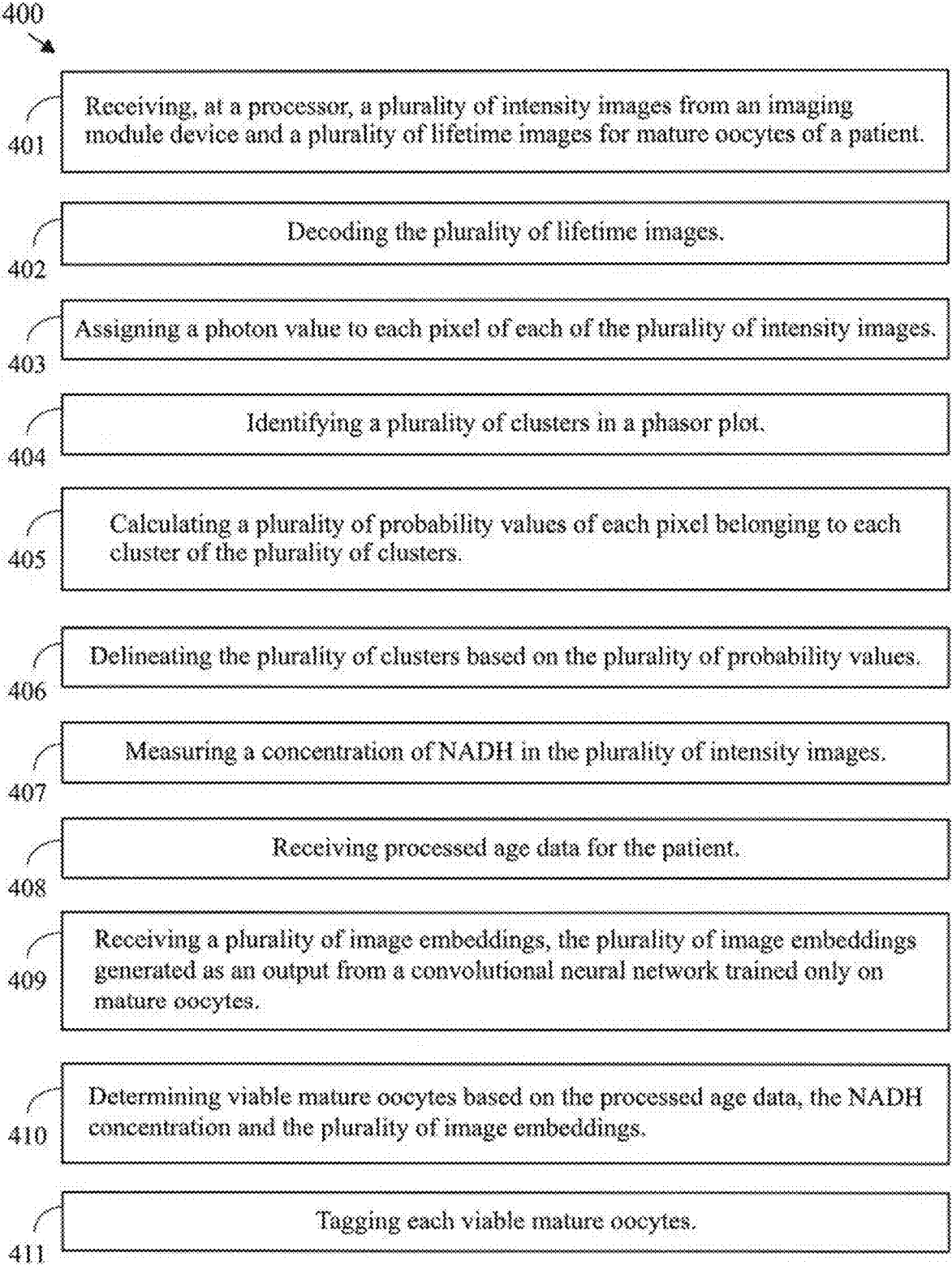

401  Receiving, at a processor, a plurality of intensity images from an imaging module device and a plurality of lifetime images for mature oocytes of a patient.

402  Decoding the plurality of lifetime images.

403  Assigning a photon value to each pixel of each of the plurality of intensity images.

404  Identifying a plurality of clusters in a phasor plot.

405  Calculating a plurality of probability values of each pixel belonging to each cluster of the plurality of clusters.

406  Delineating the plurality of clusters based on the plurality of probability values.

407  Measuring a concentration of NADH in the plurality of intensity images.

408  Receiving processed age data for the patient.

409  Receiving a plurality of image embeddings, the plurality of image embeddings generated as an output from a convolutional neural network trained only on mature oocytes.

410  Determining viable mature oocytes based on the processed age data, the NADH concentration and the plurality of image embeddings.

411  Tagging each viable mature oocytes.

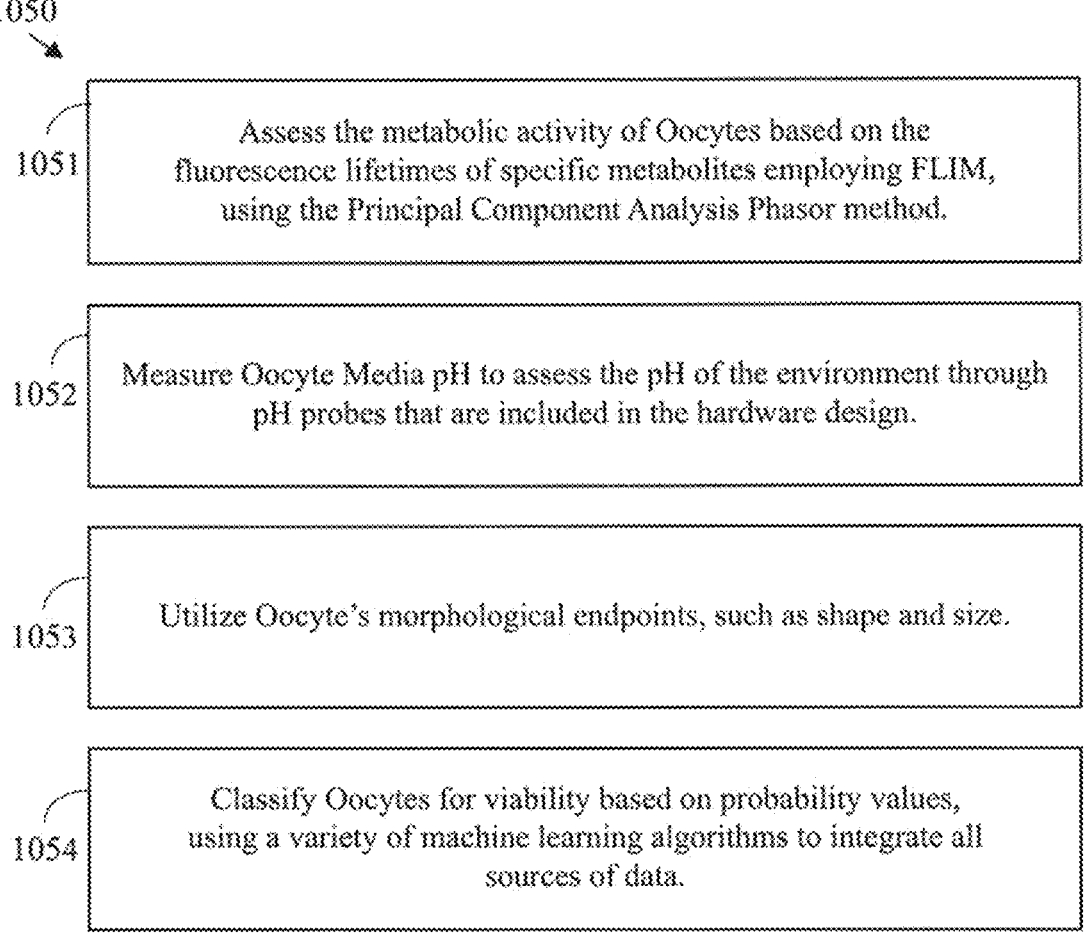

1051    Assess the metabolic activity of Oocytes based on the
fluorescence lifetimes of specific metabolites employing FLIM,
using the Principal Component Analysis Phasor method.

1052    Measure Oocyte Media pH to assess the pH of the environment through
pH probes that are included in the hardware design.

1053    Utilize Oocyte's morphological endpoints, such as shape and size.

1054    Classify Oocytes for viability based on probability values,
using a variety of machine learning algorithms to integrate all
sources of data.

FIG. 15

METHODS AND SYSTEMS FOR NON-INVASIVELY ASSESSING VIABILITY IN HUMAN OOCYTES USING METABOLIC AND MORPHOLOGICAL MEASURES

CROSS REFERENCES TO RELATED APPLICATIONS

The Present Application claims priority to U.S. Provisional Patent Application No. 63/423,902, filed on Nov. 9, 2022, and the Present Application is a continuation-in-part application of U.S. patent application Ser. No. 18/371,906, filed on Sep. 22, 2023, which claims priority to U.S. Provisional Patent Application No. 63/410,157, filed on Sep. 26, 2022, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to systems and methods to assess the viability of human oocytes.

Description of the Related Art

Since their introduction, medically assisted reproductive technologies (ARTs) have allowed millions of children to be born to infertile couples, accounting for 2% to 6% of births in Europe: results generated from European registries by Eshre: the European Ivf-monitoring consortium (Eim) for the European Society of Human Reproduction and Embryology (Eshre).

ART is generally recognized as a safe procedure that also sometimes encompasses other procedures such as egg freezing. Egg freezing could be done in two ways, egg vitrification or egg cryopreservation. Cryopreservation of oocytes by "slow freezing" was first introduced in the 1980's. However, one of the main difficulties with this technique was that oocyte survival rates remained around 60% post-thaw. That is why the introduction of oocyte vitrification has significantly improved this field. Many studies have proven that oocyte survival rates, fertilization rates, and subsequently embryonic cleavage were in fact higher after vitrification. Oocyte vitrification technology has made egg-sharing donation easier in China. Comparison of concomitant outcome achieved with fresh and cryopreserved donor oocytes vitrified by the cryotop method. Ovarian cryopreservation and transplantation for fertility preservation for medical indications: report of an ongoing experience. Efficiency of aseptic open vitrification and hermetical cryostorage of human oocytes. Oocyte vitrification in the 21st century and post-warming fertility outcomes: a systematic review and meta-analysis. Consistent and predictable delivery rates after oocyte vitrification: an observational longitudinal cohort multicentric study. How does vitrification affect oocyte viability in oocyte donation cycles? A prospective study to compare outcomes achieved with fresh versus vitrified sibling oocytes. Comparison outcome of fresh and vitrified donor oocytes in an egg-sharing donation program. Oocyte, embryo and blastocyst cryopreservation in art: systematic review and meta-analysis comparing slow-freezing versus vitrification to produce evidence for the development of global guidance.

Vitrification or "freezing" of oocytes is an assisted reproduction technique that consists of obtaining the woman's eggs and preserving them at very low temperatures (−196° C.) for an indefinite period of time in a safe and secure place. This method is used to preserve female fertility for medical reasons or in women who want to delay her motherhood.

One of the main advantages of egg vitrification is that the oocyte quality is preserved for as long as the oocytes remain vitrified. This means that the frozen eggs will have the same quality they had at the time of vitrification when the woman decides to use them for an ART procedure.

There are also many other advantages for oocyte vitrification that include: Preservation of female fertility for women who are about to undergo cancer treatment or any type of surgery that may affect their ovaries and therefore their fertility; Increased probability of ART procedure success rate if eggs are vitrified at a younger age they'll carry the same characteristics over for an ART cycle that's done when the woman is older therefore resulting in a higher pregnancy rate, as well as a lower probability of obtaining embryos with chromosomal abnormalities; Allows the accumulation of eggs through performing several ovarian stimulations and follicular punctures and vitrifying the oocytes. This mainly applies to women with low ovarian reserve and/or low responders; Better planning of IVF cycles. By using the cryopreserved donor eggs without having to synchronize the donor with the egg recipient. Oocyte vitrification has enjoyed significant usage in the context of intra-couple ART management as it is mainly used in the event of failed sperm collection. Clinical application of oocyte vitrification: a systematic review and meta-analysis of randomized controlled trials.

BRIEF SUMMARY OF THE INVENTION

One aspect of the present invention is a method to assess the viability of human oocytes for egg vitrification. The method includes receiving, at a processor, a plurality of intensity images from an imaging module device and a plurality of lifetime images for mature oocytes of a patient. The method also includes decoding the plurality of lifetime images. The method also includes assigning a photon value to each pixel of each of the plurality of intensity images. The method also includes identifying a plurality of clusters in a phasor plot. The method also includes calculating a plurality of probability values of each pixel belonging to each cluster of the plurality of clusters. The method also includes delineating the plurality of clusters based on the plurality of probability values. The method also includes measuring a concentration of NADH in the plurality of intensity images. The method also includes receiving processed age data for the patient. The method also includes receiving a plurality of image embeddings, the plurality of image embeddings generated as an output from a convolutional neural network trained only on mature oocytes. The method also includes determining viable mature oocytes based on the processed age data, the NADH concentration and the plurality of image embeddings. The method also includes tagging each viable mature oocytes.

Yet another aspect of the present invention is a non-transitory computer-readable medium that stores a program that causes a processor to assess the viability of human oocytes for egg vitrification by executing the following steps: receiving, at a processor, a plurality of intensity images from an imaging module device and a plurality of lifetime images for mature oocytes of a patient; decoding the plurality of lifetime images; assigning a photon value to each pixel of each of the plurality of intensity images; identifying a plurality of clusters in a phasor plot; calculating a plurality of probability values of each pixel belonging to each cluster of the plurality of clusters; delineating the plurality of clusters based on the plurality of probability values; measuring a concentration of NADH in the plurality of intensity images; receiving processed age data for the patient; receiving a plurality of image embeddings, the plurality of image embeddings generated as an output from a convolutional neural network trained only on mature oocytes; determining viable mature oocytes based on the processed age data, the NADH concentration and the plurality of image embeddings; and tagging each viable mature oocytes.

Yet another aspect of the present invention is a system to assess the viability of human oocytes for egg vitrification. The system includes a device connected to a microscope, a processor, and a user interface display. The processor is configured to receive a plurality of intensity images from an imaging module device and a plurality of lifetime images for mature oocytes of a patient. The processor is configured to decode the plurality of lifetime images. The processor is configured to assign a photon value to each pixel of each of the plurality of intensity images. The processor is configured to identify a plurality of clusters in a phasor plot. The processor is configured to calculate a plurality of probability values of each pixel belonging to each cluster of the plurality of clusters. The processor is configured to delineate the plurality of clusters based on the plurality of probability values. The processor is configured to measure a concentration of NADH in the plurality of intensity images. The processor is configured to receive processed age data for the patient. The processor is configured to receive a plurality of image embeddings, the plurality of image embeddings generated as an output from a convolutional neural network trained only on mature oocytes. The processor is configured to determine viable mature oocytes based on the processed age data, the NADH concentration and the plurality of image embeddings. The processor is configured to tag each viable mature oocytes.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 2A illustrates a process diagram for processing human oocytes to identify and mark viable and mature oocytes.

FIG. 2B is a continuation of FIG. 2A illustrating a part of the process diagram for processing human oocytes to identify and mark viable and mature oocytes.

FIG. 4 is a flowchart for a method to assess the viability of human oocytes for egg vitrification.

FIG. 15 is a flowchart for a method to assess the viability of human oocytes using metabolic and morphological measures.

DETAILED DESCRIPTION OF THE INVENTION

The present invention presents a novel method utilizing Fluorescence Lifetime Imaging Microscopy (FLIM) coupled with integrating an oocyte's morphological endpoints, such as shape and size, to assess and identify the viability in human oocytes. This technology is based on principles of fluorescence lifetime imaging utilizing a 2 and 3 photon microscopy and artificial intelligence (AI) to analyze the metabolic endpoints including but not limited to NADH, FAD and Tryptophan of the oocytes.

The method involves using FLIM to analyze the metabolic activity of oocytes, integrating the oocyte's morphological endpoints, and adding parental, sibling, and demographic information.

The cellular environment in an embryo and oocyte contains a complex mixture of molecular species that are indicative for metabolic state and oxidative stress such as the enzyme co-factor nicotinamide adenine dinucleotide (NAD), flavine adenine dinucleotide (FAD) and amino acid Tryptophan (Trp), in various compositions. These molecules can be probed using monochromatic light, which in turn leads to fluorescence emission in the form of visible light. The fluorescence originates at the molecules themselves and contains information from the molecule's nearest environment via its emission properties (color, lifetime, polarization, etc.). Excitation of these molecules can be accomplished optically using a microscope system either via conventional fluorescence excitation using light sources of appropriate wavelength (in the UV-A range, around 350 nm wavelength) or via non-linear absorption utilizing pulsed lasers in the near infra-red range (around 750 nm wavelength). The emission at the molecular species in the mixture is then collected with the optical microscope and detected with sensitive detectors providing data from the probed mixture. The fluorescence emission collected at each point of the embryo and oocyte reflect the complex composition of the multiple components (NAD, FAD, Trp) and it can be further analyzed either spectrally (two, three or more color detection) or in terms of the fluorescence lifetime which probes the fluorescence emission time distribution after pulsed excitation. The latter approach is part of a well-established technique termed fluorescence lifetime imaging microscopy (FLIM). FLIM data can be further analyzed using a phasor analysis approach often abbreviated phasor-FLIM.

FLIM is uniquely capable of spatially resolving temporal information. FLIM can particularly distinguish fluorophores that exhibit similar spectra; it is sensitive to the molecular environment and is independent of the fluorophore concentration. In addition, it is less vulnerable to absorption and scattering events, and does not depend on the absolute detected intensity. Therefore, FLIM measurements are precisely accurate and widely used as a very sensitive and solid microscopy method.

Figure 5A:
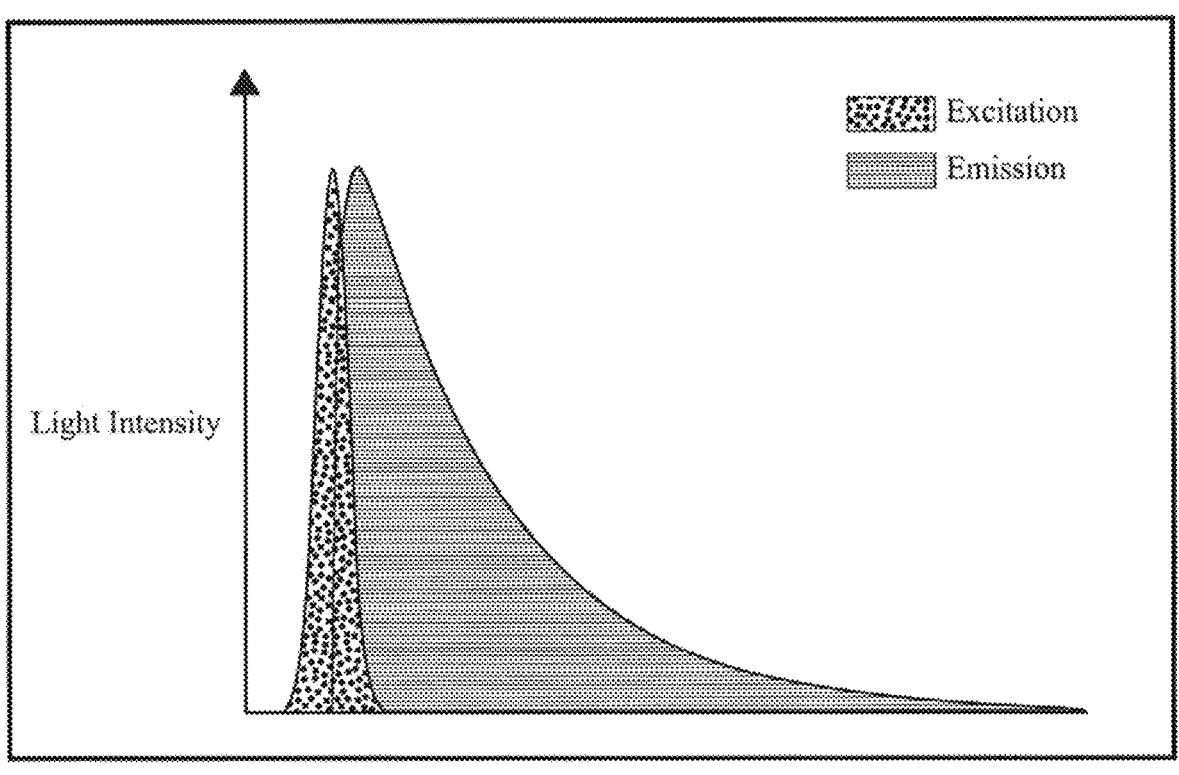
FIG. 5A is a plot of lifetime fluorescence measured by time domain method.
Figure 5B:
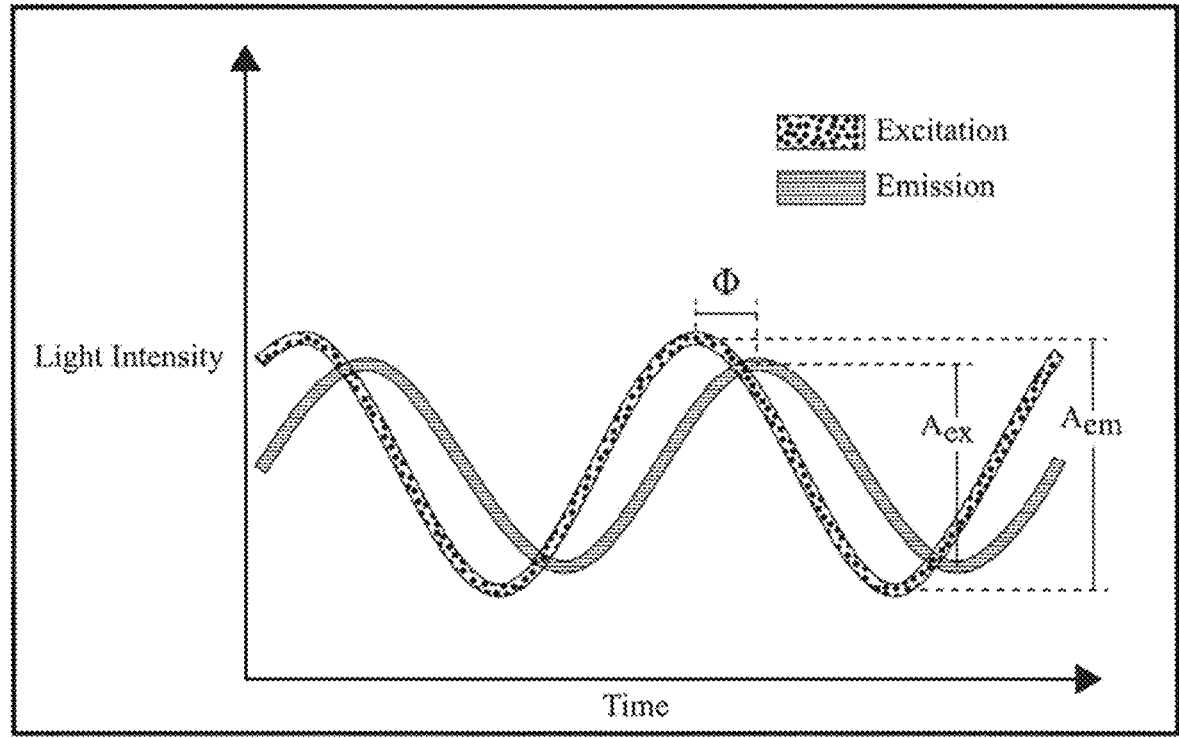
FIG. 5B is a plot of lifetime fluorescence measured by frequency domain method.

Lifetime fluorescence can be measured by either time or frequency domain methods. The time domain FLIM uses short laser pulse excitation to obtain an exponential decay corresponding to the fluorescence intensity, as illustrated in FIG. 5A. In the time domain method, an excitation light pulse is near the decay intensity of the measured photons in time. The frequency domain FLIM uses sinusoidal-modulated continuous lasers to interrogate the sample as shown in FIG. 5B. In the frequency domain method, the amplitude ($A_{ex}$, $A_{em}$) between the excitation and emission is shown, as well as the phase difference ($\Phi$) between the two light signals.

Figure 1:
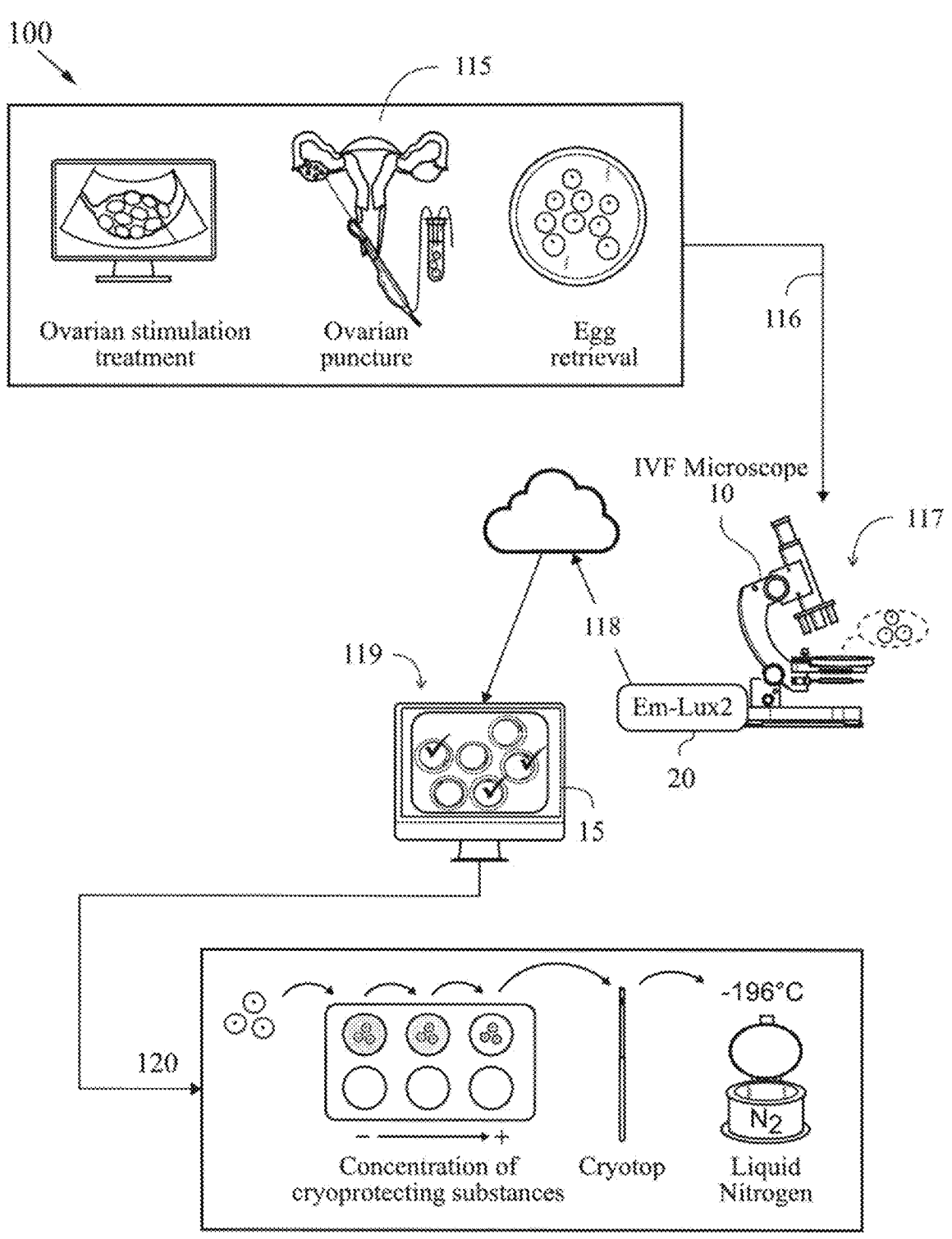
FIG. 1 is a block diagram of a system to assess the viability of human oocytes for egg vitrification.

The overall process 100 is illustrated in FIG. 1. The oocytes are retrieved through ovarian puncture 115. The oocytes are transported 116 to a microscope 10 equipped with an Em-Lux 20 module or an Em-Lux 20 stand-alone imaging device. The oocytes are imaged 117 for fluorescence lifetime signal along with brightfield imaging to assess both functional and structural endpoints. All data, including but not limited to what's acquired in the previous step, are sent 118 through a cloud-based infrastructure for AI processing-algorithms for analyzing the viability of the oocytes and for classifications of Aneuploid vs. Euploid ones. Euploid oocytes are tagged 119 and recommended to be crypto-protected 120 for future fertilization needs.

Figure 3:
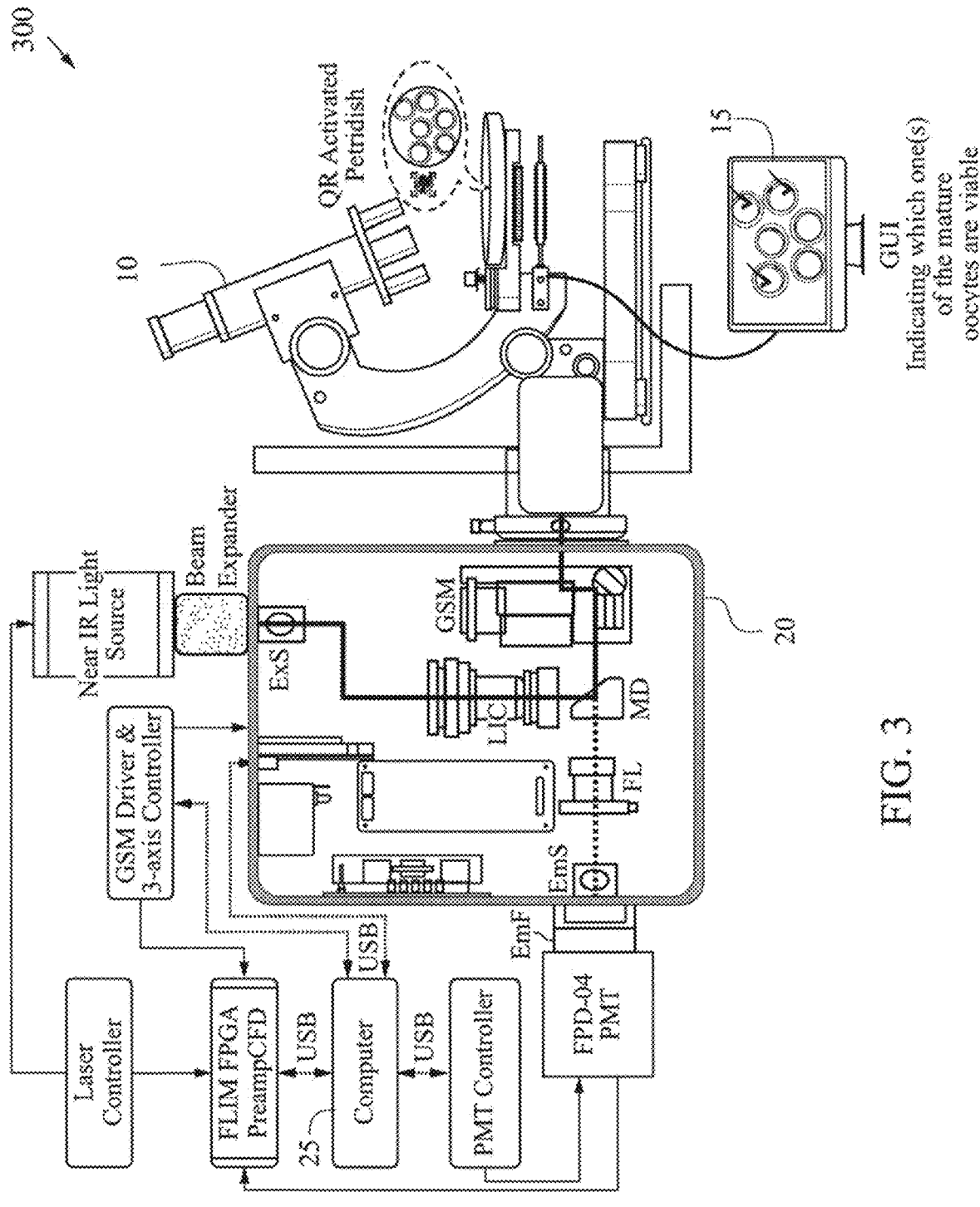
FIG. 3 is a block diagram of a system to assess the viability of human oocytes for egg vitrification.

FIG. 3 illustrates a preferred system 300 to assess the viability of human oocytes for egg vitrification. The system 300 comprises a device (Em-Lux2) 20 connected to a microscope 10, a processor 25, and a user interface display 15. The Em-Lux2 20 takes over the light source and the detection system. Em-Lux2 20 captures both intensity images and fluorescence lifetime measurements.

The processor 25 is configured to do the following: receive intensity images from an imaging module device and lifetime images for mature oocytes of a patient; to decode the lifetime images; to assign a photon value to each pixel of each of the intensity images; to identify clusters in a phasor plot; to calculate probability values of each pixel belonging to each cluster of the clusters; to delineate the clusters based on the values; to measure a concentration of NADH in the intensity images; to receive processed age data for the patient; to receive image embeddings, the embeddings generated as an output from a convolutional neural network trained only on mature oocytes; to determine viable mature oocytes based on the processed age data, the NADH concentration and the image embeddings; and to tag each viable mature oocyte.

FIGS. 2A and 2B illustrate a process diagram for processing human oocytes to identify and mark viable and mature oocytes. The process 200 is designed with minimum disruption in the existing process as this method will only add a few minutes to quantify NADH intensity obtained with FLIM and will help embryologists identify viable embryos and only transport those to the remaining pipeline.

At a first stage of the process 200, data acquisition and encryption, data is obtained through Em-Lux, either as a stand-alone device or an add-on to an IVF microscope. To ensure privacy and security, the acquired data undergoes local storage, image, and patient data encryption and anonymization processes. This guarantees the confidentiality of patient information and maintains the integrity of the data.

At a second stage of the process 200, assessing patient demographic and siblings data, patient demographic data, including age, medical history, and current medications, is collected, anonymized, and encrypted. Additionally, parental siblings' information, such as the number of males vs. females and twins, is gathered. This comprehensive dataset provides valuable context for the analysis.

A third stage of the process 200 includes assessing metabolic endpoints with FLIM. Photon Lifetime Decay Analysis: Raw photon lifetime decay data is processed to create a 2D heatmap, revealing patterns and variations in metabolic endpoints. Phasor Plot Decoding: A novel phasor plot analysis is applied to high-quality oocytes. Principal component analysis and Phasor method are used to extract meaningful information, aiding in data understanding. Visualization through Plots: Multiple 2D and 3D plots are generated to visualize the distribution of data across different Z-planes. Identified clusters are studied for their metabolic characteristics. Feature Extraction: Variables are extracted from phasor plot density contours, enabling a detailed understanding of the metabolic endpoints. Advanced Analysis: Component analysis, PCA, and higher (ie 3rd) harmonic analysis are performed to refine data classification, enhancing the accuracy of metabolic endpoint assessment.

At a fourth stage of the process 200, collecting oocyte media pH, pH values are collected from the oocyte media. Each pH value is assigned a numerical representation based on whether the conditions are acidic or basic. This numeric data provides insights into the chemical environment surrounding the oocytes.

A fifth stage of the process 200 includes collecting and analyzing numerical values for morphology assessment. Image Preprocessing: Images are preprocessed by filtering out low-quality, blurred, and empty images. Background removal and automatic segmentations enhance the quality of images for analysis. Expert Grading: Embryologists grade the preprocessed images, providing ground truth labels for training machine learning models. Deep Learning Models: Convolutional Neural Networks (CNNs) such as ResNet, EfficientNet, and Inception are applied to score morphological features of oocytes. These models learn intricate patterns and features from the images. Qualitative Assessment: Oocyte scores generated by deep learning models are combined with embryologists' scores, providing a comprehensive qualitative assessment of oocyte morphology.

At a sixth stage of the process 200, data integration and classification, data from the different pipelines are integrated for the final classification stage. Various deep learning models, including Long Short-Term Memory networks (LSTMs), are employed. These models are trained on the integrated dataset and tested on different classification tasks, such as distinguishing between aneuploid and euploid oocytes. Classification tools like XGBoost are utilized to assign probabilities to oocytes, tagging them based on the highest probabilities for positive class (euploids).

At a seventh stage of the process 200, results interpretation, the final outcome includes the classification of oocytes into aneuploids and euploids. Additionally, within the euploid cohort, oocytes are ranked based on their viability probabilities, providing valuable information for further clinical decision-making in the context of assisted reproductive technologies.

This comprehensive and sophisticated approach ensures a detailed analysis of oocyte viability, incorporating multiple data sources and advanced analytical techniques to provide accurate and meaningful results for clinical applications.

An Intensity+Fluorescence Lifetime+Demographic based algorithm is alternatively used to fully assess the viability of mature oocytes. Human oocytes are cultured on the QR-enabled devices and then sent over to be imaged under the existing microscopes. The oocytes will undergo a pre-processing step where trained embryologists would carefully look at their morphological characteristics to identify mature eggs, these are labeled as M2. Once M2 oocytes are identified, they'll be imaged using an Em-Lux2 module that's connected to the microscope. The Em-Lux2 will capture both intensity data (this will be the brightfield images) and the fluorescence lifetime data. Intensity images will undergo a cloud-based image embedding processing where they'll be normalized first to remove any inherent noise or artifacts across the dataset. The M2s will then be undergo a shallow convolutional neural network (CNN) processing. In this step, all morphological endpoints such as shape, size, and intensity will be extracted to be fed into the classification algorithm down the pipeline.

In parallel, the algorithm used to fully assess the viability of mature oocytes will assess the functional and metabolic endpoints from the lifetime signal. In this step lifetime files are decoded from the dataset and each pixel on the intensity image will be assigned a photon value. Fourier transformation on images will be performed to obtain the spectral-phasor coordinates. A clustering algorithm, such as the Gaussian Mixture Model will be run, assuming that the data points are Gaussian distributed which is a less restrictive assumption compared to the ones in other clustering algorithms. Then an optimized algorithm will be used, such as expectation maximization, to further process the datapoints. At this point, the NADH intensity is identified using reference data.

Patient demographic data such as age is also processed in this algorithm. The age is divided into distinct categories since the quality, and therefore the viability, declines at a certain age. Age cohorts of under 35, =36, =37, =38, =39, and 40 and over are in separate categories. Using the One-Hot encoding method, categorical features are extracted. At this point, the XGBoost classification algorithm is used on features and datapoints extracted from image embeddings, metabolic endpoints (NADH) and age in order to calculate a viability score on M2 oocytes. Once calculated and identified, mature M2s are reported to the embryologists or the end-user using a simple graphical user interface (GUI) by putting checkmarks on them.

Figure 6:
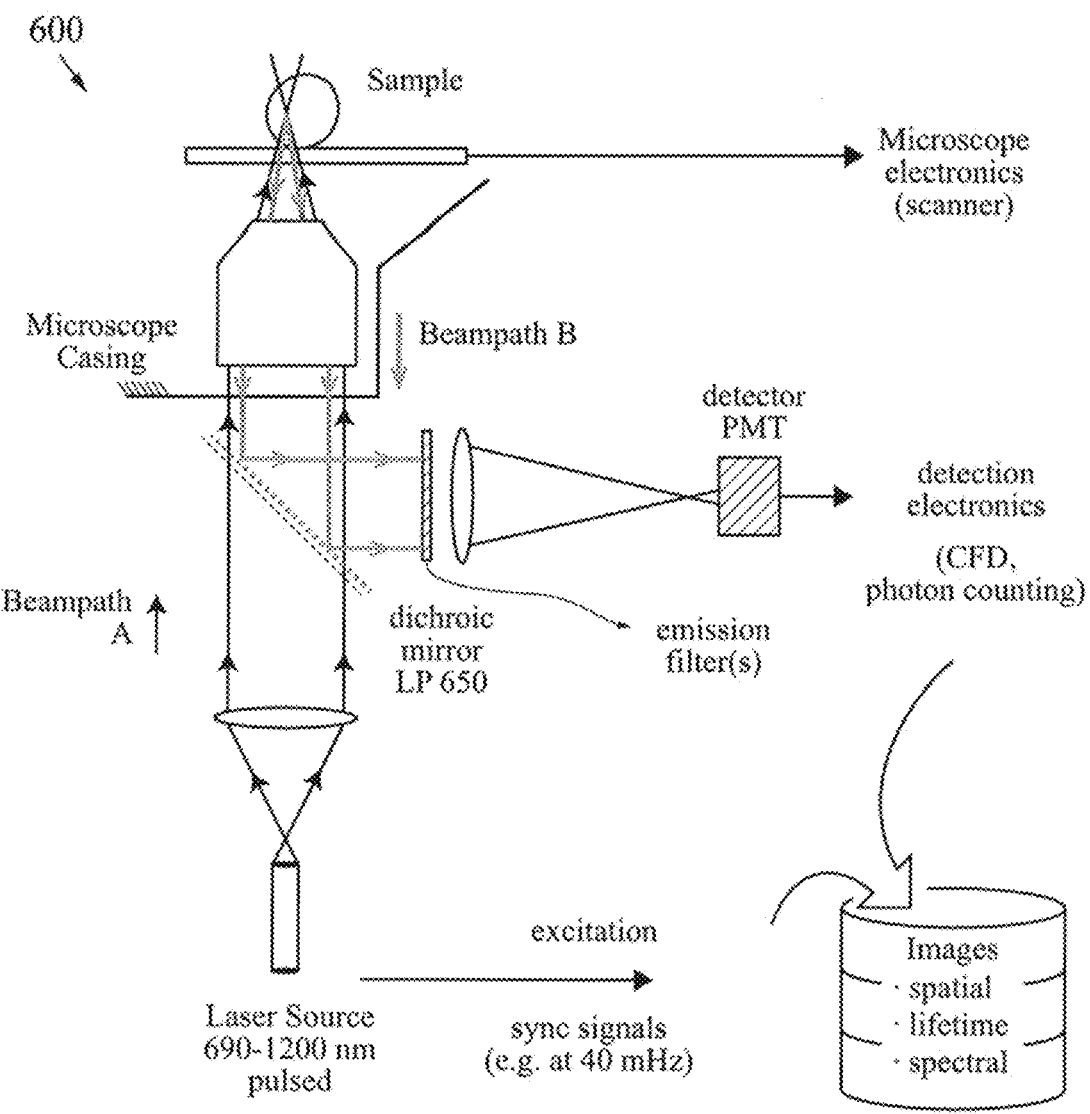
FIG. 6 is a block diagram of an optical setup to assess the viability of human oocytes for egg vitrification.

FIG. 4 is a flow chart for a method 400 to assess the viability of human oocytes for egg vitrification. The method comprises receiving, at a processor, a plurality of intensity images from an imaging module device and a plurality of lifetime images for mature oocytes of a patient at step 401. Step 402 is decoding the plurality of lifetime images. Step 403 is assigning a photon value to each pixel of each of the plurality of intensity images. Step 404 is identifying a plurality of clusters in a phasor plot. Step 405 is calculating a plurality of probability values of each pixel belonging to each cluster of the plurality of clusters. Step 406 is delineating the plurality of clusters based on the plurality of probability values. Step 407 is measuring a concentration of NADH in the plurality of intensity images. Step 408 is receiving processed age data for the patient. Step 409 is receiving a plurality of image embeddings, the plurality of image embeddings generated as an output from a convolutional neural network trained only on mature oocytes. Step 410 is determining viable mature oocytes based on the processed age data, the NADH concentration and the plurality of image embeddings. Step 411 is tagging each viable mature oocytes FIG. 6 illustrates a preferred optical setup 600 of the present invention.

The optical setup comprises of light sources that excite NADH, FAD, Trp; detectors that capture the fluorescence lifetime emission of NADH, FAD, and Trp; a solid-state detector (or a probe-detector-electronics interface) that determines the supernatant acidity (pH meter), temperature, and conductivity (either directly or via aliquot); mechanical parts; cameras (CCD or CMOS); a panel PC (a processor); and electrical parts.

The preferred setup uses two separate light sources to excite different fluorophores. One light source is preferably a pulsed near-infra red laser with a wavelength in the range between 680 and 1000 nm. The pulse repetition rate is preferably in the range between 20 and 80 MHz. Pulse widths (for non-linear optical excitation) is preferably in the range between 50 and 500 fs (femtoseconds). Additionally, another light source is a pulsed or modulated UV-A laser with a wavelength in the range between 300 and 420 nm, a pulse repetition rate or modulation frequency between 20 and 80 MH, and pulse widths shorter than 1 ns (equivalent to 1 GHz).

NADH and FAD are excited at wavelengths around 355 nm and emit fluorescence in a peak from 400 nm.

NADH and FAD (excitation: 355 nm, emission around 400 nm).

Tryptophan is excited at wavelengths around 280 nm and emits fluorescence in a peak from 300 nm.

The detectors that capture the fluorescence lifetime emissions are photon counting detectors with precise photon detection time-signatures, such as time correlated single photon counting (TCSPC). The detectors are preferably sensitive photodiodes, such as avalanche photodiodes (APDs), hybrid detectors (HyD), or fast GaAsP photodetector tubes, in combination with fast analog-to-digital conversion electronics, for example, constant fraction discriminators, pulse generators, pulse pickers, pulse generators, etc.

The solid-state detector is preferably an ion-sensitive field-effect transistor (ISFET) or of an equivalent based technology in which the front sensor is built-in or part of the sterilized (or sterilizable) receptacle in which the oocyte is situated. This sensor is in contact with the media surrounding the oocyte. The pH detector probe preferably also measures temperature and conductivity, which is an indicator for salinity, ion strength, etc.

The mechanical parts preferably includes a microscopy apparatus with actuators (motors and mechanisms) to allow for sample handling and moving as well as digital interfacing with imaging electronics; a sample loading and documenting (e.g., bar-code reader) part or a solvent dispensing part; an anti-vibration surface (passive or active) on which equipment is mounted; and an incubation and environmental control, also for shielding of external influences, such as room light, temperature variations, gas flow from A/C, etc.

The CCD or CMOS cameras are for scanning barcodes and overview images on the petri-dish.

The electrical parts include power supplies (high voltage for detectors and lasers); thermal elements and fans for incubation; and power supplies (regular voltage), communication interfaces and power distribution for actuators, lamps, and motors.

This microscopy setup, the system described above, will acquire images and at the same time acquire different fluorescence parameters in order to generate data that will be used to determine oocyte viability. The samples must not be stained or otherwise modified as the intrinsic properties from molecular species in the cells alone are responsible for the detected signal. Furthermore, the setup will use non-linear optical methods (e.g. two- and three-photon absorption) as a further way to minimize the excitation volume (e.g. for 3-D probing and also to move the excitation energy from UV to infra-red wavelengths). The setup consists of two beam paths, one for excitation and one for detection. The excitation beam path (Beampath A in FIG. 6) routes the pulsed near-infrared laser (of about 800 nm wavelength) into the microscope casing through the microscope's coupling ports. It is focused into the sample. At the focal spot (which is a small ellipsoid volume of about 400 nm in lateral width and about 1500 nm along the excitation axis) the nonlinear optical effects (two- and three-photon absorption) take place causing the molecules to emit fluorescence. The fluorescence is in the visible range, from 350 nm to about 600 nm in wavelength, which makes it easy to separate the fluorescence light from the excitation light using a dichroic mirror which reflects only light below 650 nm. This fluorescence detection beampath (Beampath B in FIG. 6) is routed through further optics to (a) further refine the spectral detection window using emission filters and (b) focus onto the detector which produces detection pulses upon the arrival of the fluorescence. The electronics (microscope controls, detection and excitation electronics) are then coupled together to produce images, comparing the narrow excitation pulses that are produced by the laser hardware and the comparatively broad detection pulses from the fluorescence that arrive with a slight delay due to the photophysical properties of the molecules in the specimen (fluorescence lifetime).

Altogether, this results in an image that contains spatial information (morphometric data like sizes and shapes of cells, for example), spectral information (e.g., the proportion between emission colors of different compounds in the cells), and lifetime information (e.g., the photophysical properties of the same compounds that are sensitive to the cell's metabolites).

The aforementioned absorption and emission processes are highly sensitive to the environment nearest of the molecules. These processes are affected by a number of factors, especially acidity (pH values) and the presence of heavy ions (iron or calcium) in the near field of the molecules. Moreover, these processes are also affected by intramolecular properties, e.g., if they are in a relaxed conformation or embedded in a rigid structure such as protein or lipid rich compartment, that are present in the cell. Altogether, these influences cause the molecules to absorb and emit light within slightly different energy bands (i.e. their emission spectra), slightly different efficiencies (making the fluorophores appear brighter or dimmer in proportion to each other), and slightly different fluorescence delay times. Together these parameters from thousands of molecules in the cells can produce a signature fingerprint in its combined emission spectrum, intensity proportions and fluorescence lifetime. This is what is ultimately exploited to determine differences in the metabolic state and the inner composition of the cells.

Steps involved in quantifying metabolic endpoints:

The mathematical processes used in quantifying metabolic signatures from the phasor plot is presented.

The fluorescence signal from captured data is transformed according to the following Fourier transformations that allows a switch in the computation from time domain to frequency domain:

$$s_i(\omega) = \frac{\int_0^\infty I(t)\sin(n\omega t)dt}{\int_0^\infty I(t)dt}, \, g_i(\omega) = \frac{\int_0^\infty I(t)\cos(n\omega t)dt}{\int_0^\infty I(t)dt}$$

Where $s_i(\omega)$ and $g_i(\omega)$ are the y and x coordinates in the phasor plot, $\omega = 2\pi f$ where f is the repetition frequency of the laser source and n is the harmonic frequency.

Performing this transformation brings the representation of the signal in the two dimensional space called "phasor plot". Different positions of the signal in the phasor plot identify different metabolic conditions of the sample.

The phasor plot is therefore populated by a number of points that aggregate in clusters around an area of significance and a better representation of the data is reached if the points are aggregated in a two dimensional histogram. The histogram representation gives information on the number of points that fall in a specific unit cell and hence on the relative "phasor plot intensity" of the signal in a specific area.

Figure 7:
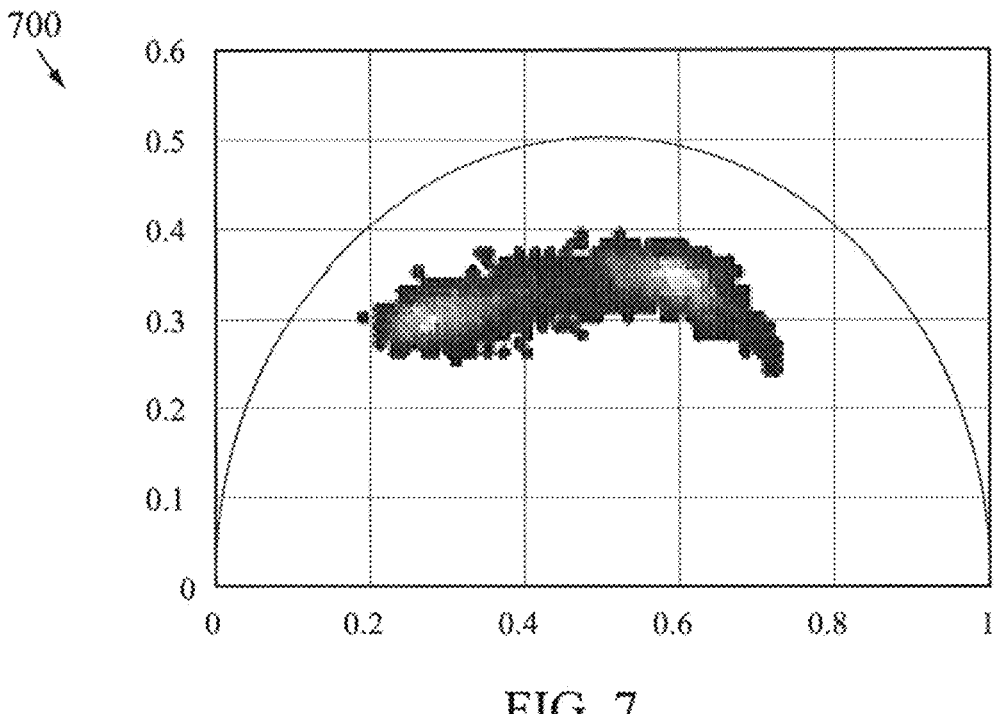
FIG. 7 is a phasor plot of an oocyte.

In FIG. 7, the plot 700 is an example of the representation of the fluorescence signal in the phasor plot for one oocyte: where the axis are the g and s coordinates. It is easy to note that there are two areas of aggregation for the points in the phasor plot. The two clusters identify different parts of the oocyte and they can be separated with some clustering algorithms.

Figure 8:
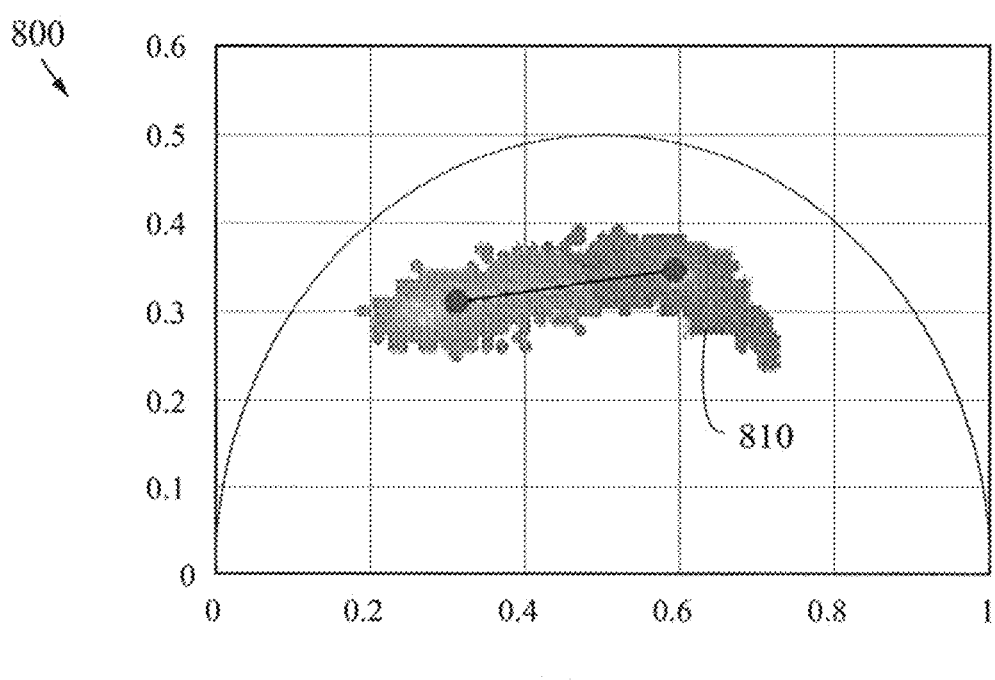
FIG. 8 is a phasor plot of FIG. 7 with a Gaussian Mixture Model applied.
Figure 9:
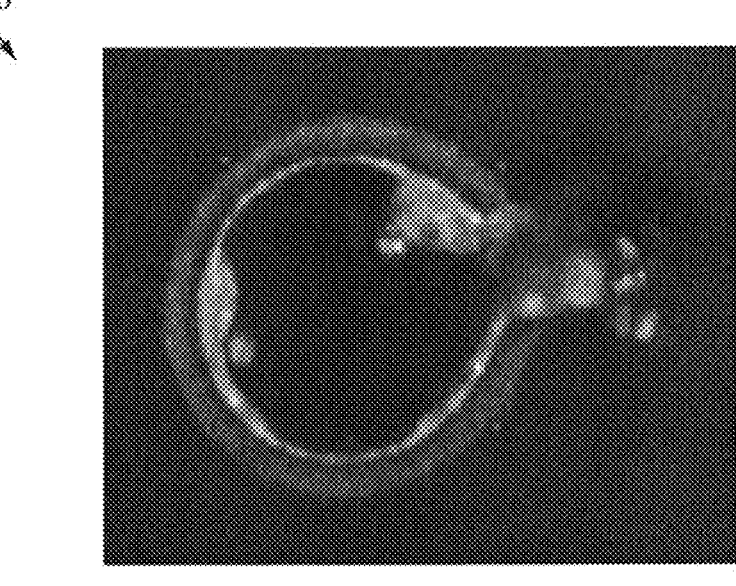
FIG. 9 is an image of an oocyte.
Figure 10:
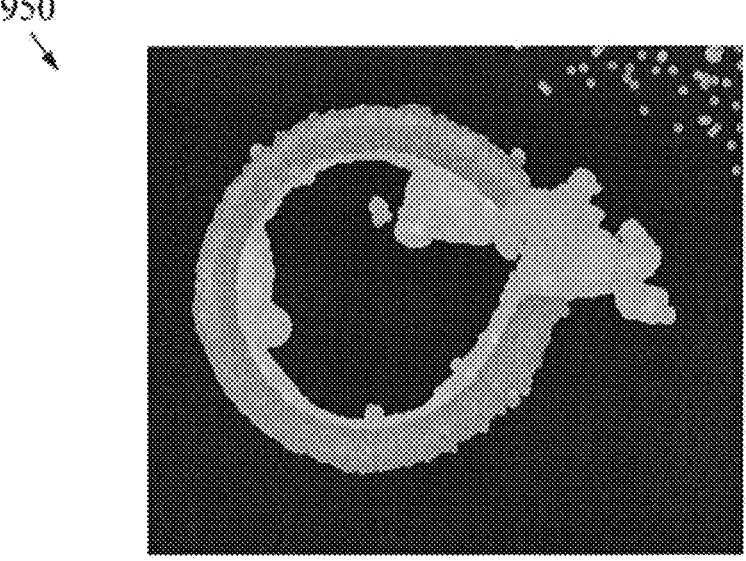
FIG. 10 is an image of an oocyte of FIG. 9 with a Gaussian Mixture Model applied.

In FIG. 8, the plot 800 shows a result of using a Gaussian Mixture Model for the separation. When applied to the initial image 900 of the oocyte, as shown in FIG. 9, the clusters show the different areas of origin, as shown in the image 950 of FIG. 10.

In this analysis, the Inner Cell Mass of the oocyte is considered to be crucial for the evaluation of the oocyte health. Therefore, in the following analysis, what appears to be the right hand cluster 810 in the phasor plot for each oocyte is taken into consideration.

Interesting quantities that characterize the clusters in the phasor plot and that can help identify differences between different metabolic conditions are: the center of momentum—average coordinates g and s; the angle of the line that joins the axis origin and the center of momentum; and the two axis of the cluster that give the shape of the cluster "cloud" in terms of rotation and length.

In particular, the above mentioned quantities are calculated according to the following formulas:
Center of Momentum:

$$g_M = \frac{\sum_{i=1}^N I_i g_i}{\sum_{i=1}^N I_i}, \, s_M = \frac{\sum_{i=1}^N I_i s_i}{\sum_{i=1}^N I_i}$$

where i is the index of each unit cell of the histogram and N is the total number of unit cells, with $I_i$, $g_i$, and $s_i$ being the respective intensity and coordinates.

11

Angle:

$$\vartheta = \arctan\left(\frac{g_m}{s_M}\right) * \frac{180}{2\pi}$$

Axis:

$$V_{ic} = \frac{2 * \sqrt{e_i} * v_{ic}}{\sum_{ic} v_{ic}^2}$$

where e and v are the eigenvalues and eigenvectors computed by iterative process, i identifies the axis (it can be zero or one), c is the coordinate (g or s).

Another interesting quantity that can be derived from the phasor plot is the Metabolic Index (MI). With the tau phase and modulation values for the oxidation and glycolic states ($\tau_{ps}$, $\tau_{ms}$, where s labels the state), (to be respectively $3.4*10^{-9}$ e$0.4*10^{-9}$) and the k value computed as:

$$k = \frac{1}{2 * \pi * n_{harmonic} * fex}$$

Where fex is the repetition rate of the laser source, and $n_{harmonic}$ is the number of the harmonic frequency. For each state (oxidation, glycolic) the following quantities are then computed:

$$\varphi_s = \arctan(\tau_s / k)$$

$$m_s = \sqrt{\frac{1}{1 + \frac{\tau_{ms}}{k^2}}}$$

$$g_s = \frac{m_s}{\cos(\varphi_s)}$$

$$s_s = \frac{m_s}{\sin(\varphi_s)}$$

where $g_s$ and $s_s$ are the coordinates of the points that identify the states in the phasor plot. The MI can then be computed by taking the coordinates of the intersection of the line that goes by the two states and the line that goes by the center of momentum and the origin of the phasor plot and then calculate how far the intersection is from each of the two state points. For instance, with the label of the line intersection as ($g_i$, $s_i$) and ($g_o$, $s_o$), ($g_g$, $s_g$) the coordinates of the oxidation and glycolic points respectively, then the MI can be calculated according to the following formula:

$$MI = \frac{\sqrt{(g_g - g_i)^2 + (s_g - s_i)^2}}{\sqrt{(g_g - g_o)^2 + (s_g - s_o)^2}}$$

Figure 11:
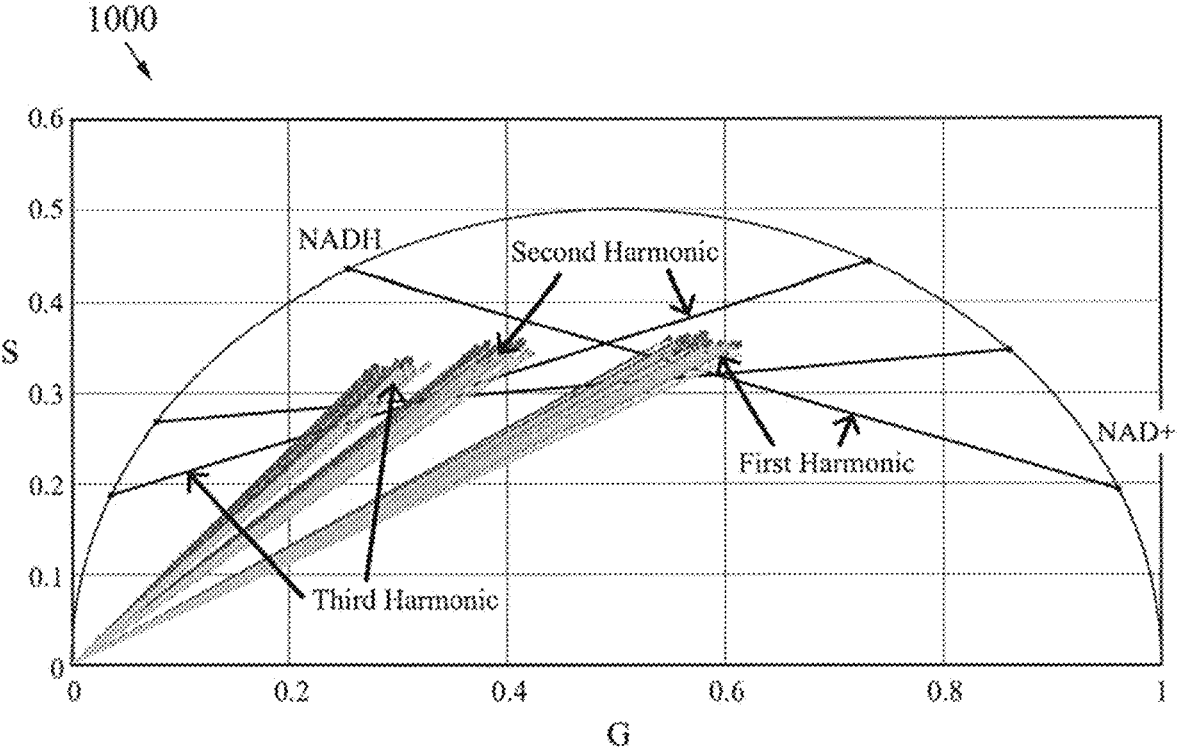
FIG. 11 is a plot of the projections of the centers of momentum to the metabolic index line in the first harmonic, the second harmonic and the third harmonic for different samples.
Figure 12:
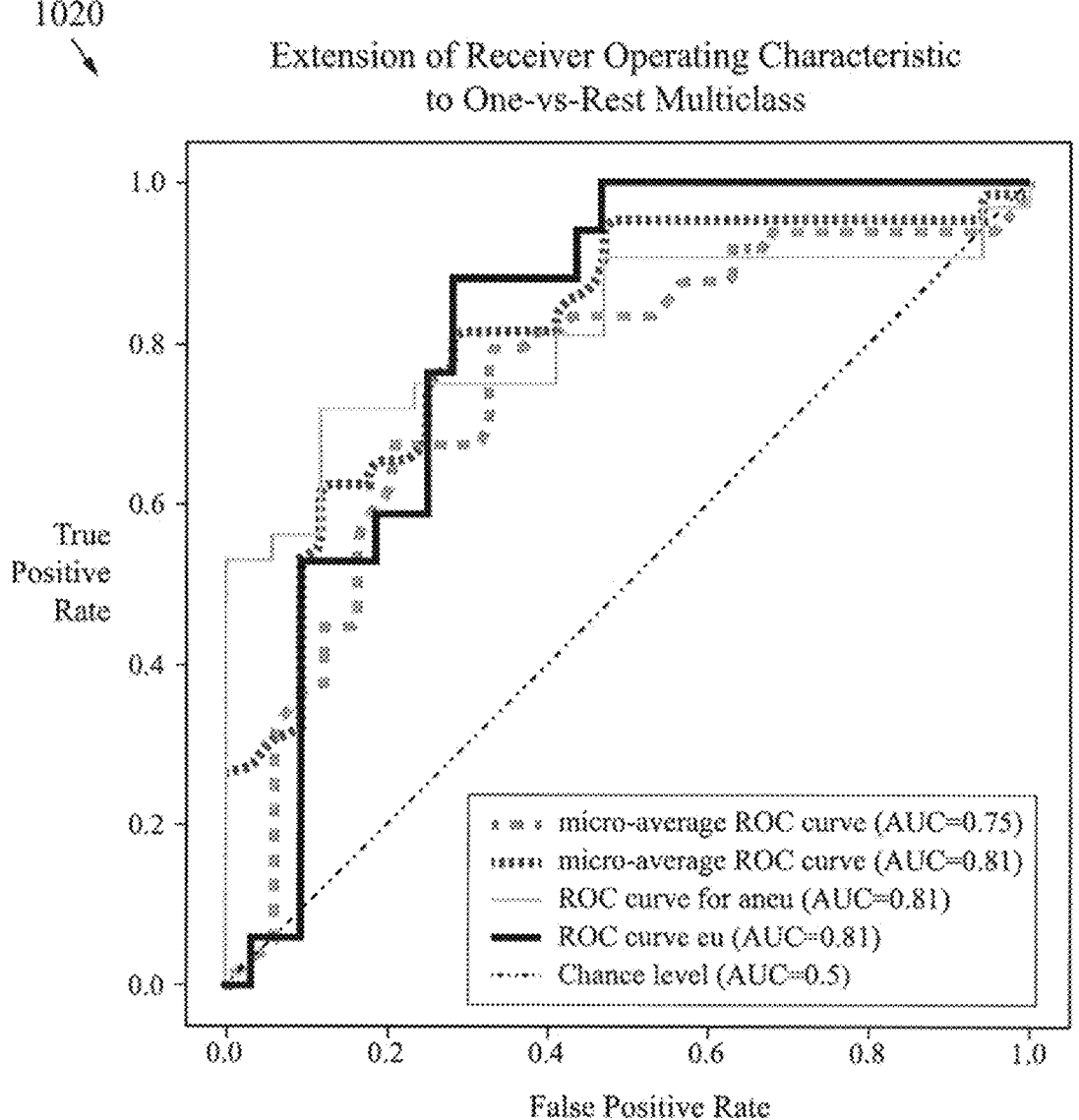
FIG. 12 is a graph of true positive rate vs false positive rate for a first harmonic.
Figure 13:
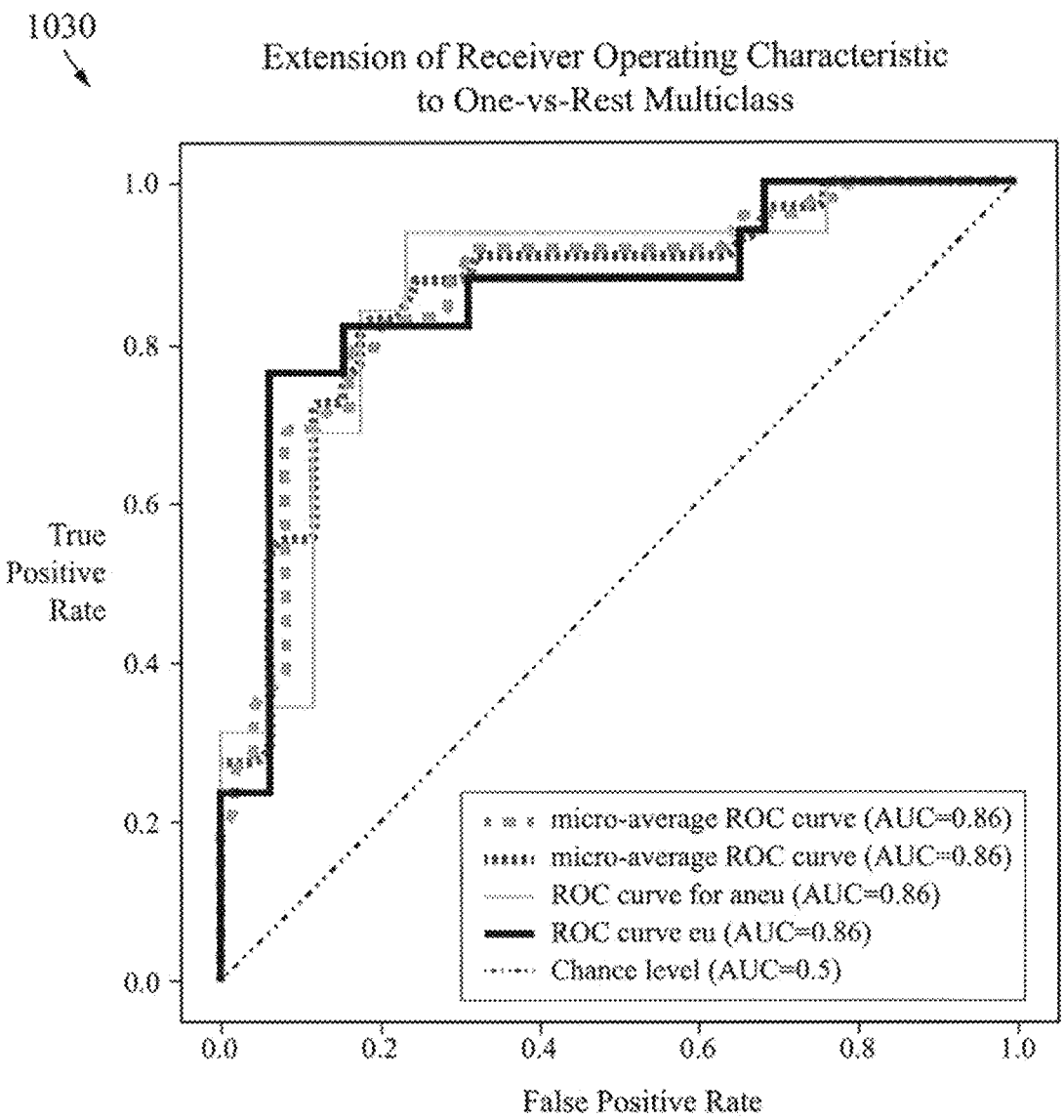
FIG. 13 is a graph of true positive rate vs false positive rate for a second harmonic.
Figure 14:
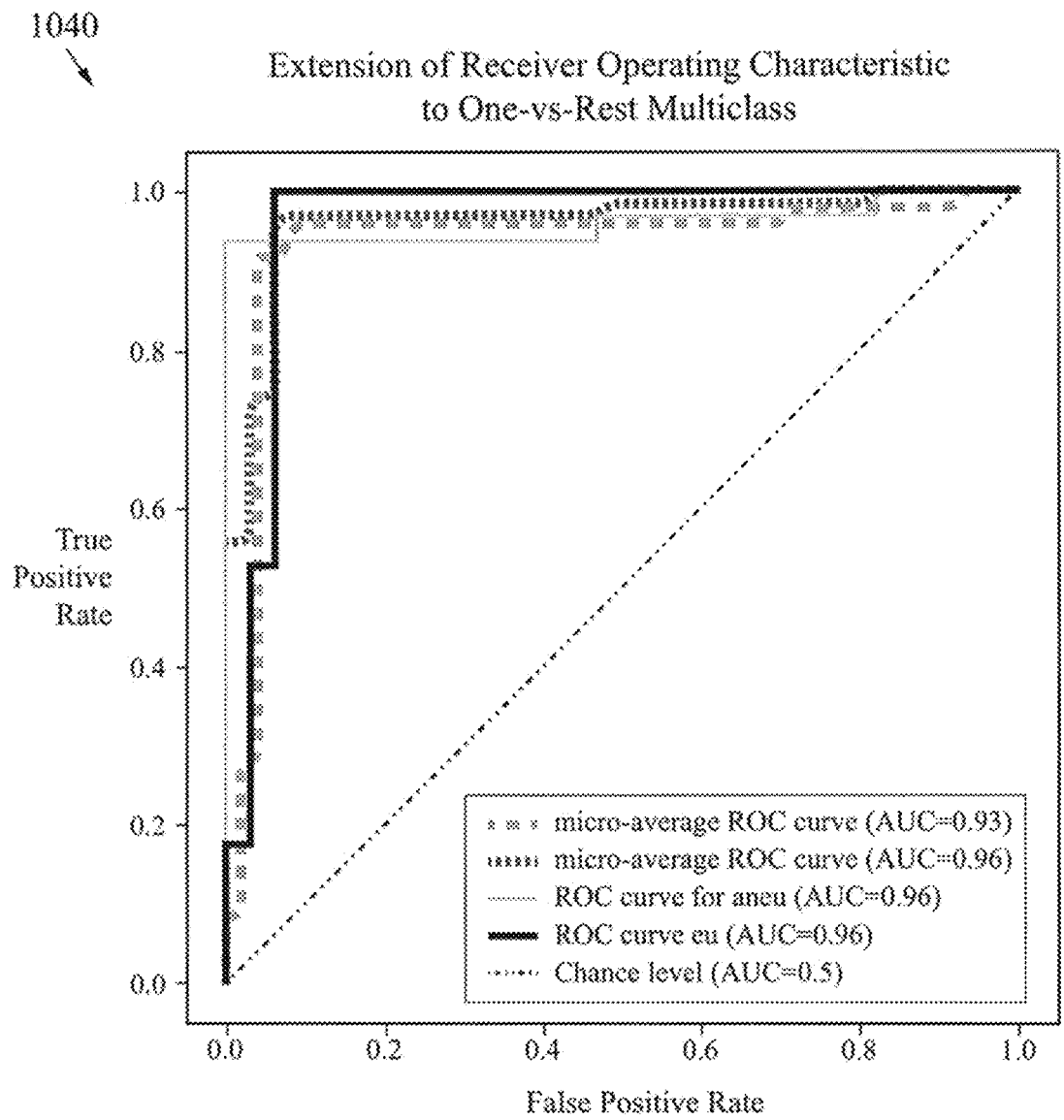
FIG. 14 is a graph of true positive rate vs false positive rate for a third harmonic.

To clarify how the MI is calculated, the plot of the projections of the centers of momentum is added to the MI line in the first harmonic, the second harmonic, and the third harmonic for different samples, as shown in FIG. 11.

Thus, four layers are taken into consideration and computed: center of momentum (2 coordinates), angle, axis (2 coordinates), and MI.

Therefore, there are six quantities (or "features" in machine learning specific language) that can be analyzed to better characterize an oocyte's metabolic state. Calculating all the features for the four layers results in 24 features that characterize each oocyte. Therefore, a model is needed to separate the two populations and optimize the combination of the features so that the separation is maximized.

Optimization

70% of the population is taken as a training set preserving the relative percentage of each population from the whole samples to the training set. The following quantities are considered for the training set:

Distance of each feature (k) for each sample (i) from the mean value of the given feature across the alike population. The division by the max of the distance normalizes the values from 0 to 1 so that the future optimization will be balanced. This is called positive distance.

$$D_{pki} = \frac{f_{kic} - p_k}{\max(f_{kic} - p_k)}$$

Distance of each feature for each sample from the mean value of the given feature across the other population. This is called negative distance.

$$D_{nki} = \frac{f_{kic} - n_k}{\max(f_{kic} - n_k)}$$

The solution is then found for the following set of equations:

$$D = \min\left(\sum_{k=1}^{24}\left(\sum_{i=1}^{N} \text{abs}(D_{pki})w_k + \frac{1}{\sum_{i=1}^{N} \text{abs}(D_{nki})w_k}\right)\right)$$

$$0 \le w_k \le 1$$

$$\sum_{k=1}^{24} w_k = 12$$

With these equations, the following goals are achieved:

The global distance of each sample is minimized from the class that it belongs to by a sum of the actual distance from the class and the inverse of the distance from the other class. While intuitively subtracting the negative distance and optimizing for negative values, the inverse here gives the right weight to the situation where a sample is close to the boundary of its own class, so far from the means, in the opposite direction from the other class. In practice, the second term vanishes in this situation, creating a typical "repulsive" behavior. The same is observed for a sample that has values in between the two classes, in this situation the second term becomes predominant.

The weight boundaries enforce normalization for the different features.

The fixed sum produces a balancing of the weights where at least some of them have to be relevant for the classification. The case where every feature has the same importance implies that every weight is 0.5.

From the computational point of view, the optimal combination of the weights is found by performing the minimization with a Sequential Least Squares Programming algorithm that is run until convergence.

The result shows that a large part of the weight is put on the s coordinate of the center of momentum, the angle and the Metabolic Index. This process is performed to identify various metabolic signatures from raw fluorescence lifetime data that's captured by the microscope.

Evaluation

To evaluate the reliability of the model and the effectiveness of the optimization, consider the test batch of the sample which corresponds to 30% of the total number of samples. Then calculate the Separation Index (SI) of each sample according to the following formula:

$$\frac{\sum_{k=1}^{24} (\text{abs}(D_{aki})w_k - \text{abs}(D_{eki})w_k)}{\sum_{k=1}^{24} (\text{abs}(D_{aki})w_k + \text{abs}(D_{eki})w_k)}$$

where $D_{aki}$ and $D_{eki}$ are the distances from the aneuploid and euploid classes respectively for each feature. In practice, the value of the Separation Index can be between $-10$ and $10$, where $-10$ indicates that a sample belongs to the aneuploid family while a value of 10 to the euploid family. Each value in between has to be considered as probability that the sample belongs to one or the other class.

The above procedure is performed for each harmonic, being the third harmonic the one that gives the best results. The overall accuracy of the model is around 91%, with a remarkable 93% for the third harmonic. This is a remarkable result that can be better visualized with the ROC curves.

Here cyan and orange curves are the ones for aneuploids and euploids with respect to the other class and the dotted lines are two different ways of performing the average of the two, namely in the micro and macro environment.

The value of AUC (Area Under the Curve) for the ROC plot above 0.9 are considered outstanding, which validates the appropriateness of the model for an automatic discrimination between euploids and aneuploids.

FIG. 15 is a flowchart for a method 1050 to assess the viability of human oocytes using metabolic and morphological measures. At block 1051, the metabolic activity of oocytes is assessed based on a plurality of fluorescence lifetimes of specific metabolites of the oocytes generated by fluorescence lifetime imaging microscopy (FLIM) using a principal component analysis phasor method on a FLIM microscopy apparatus. At block 1052, oocyte media pH is measured to assess the pH of the environment through a plurality of pH probes. At block 1053, oocyte's morphological endpoints comprising shape and size from the spatial information is utilized. At block 1054, machine learning algorithms are used to integrate all sources of data and classify the oocytes for their viability based on a plurality of probability values.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

14

We claim as our invention the following:

1. A method for viability assessment in human oocytes, the method comprising:
placing a plurality of oocytes within a microscope with an imaging module;
focusing a pulsed near infrared laser having an excitation wavelength in a range from 680 nanometers (nm) to 1000 nm at the plurality of oocytes for 2 and 3 photon absorption to cause the plurality of oocytes to emit fluorescence light, wherein the fluorescence light is in the visible light range ranging from 350 nanometers (nm) to 600 nm;
separating the fluorescence light using a dichroic mirror to reflect fluorescence light below 650 nm;
routing the reflected fluorescence light below 650 nm through a spectral detection window comprising a plurality of emission filters to generate a refined fluorescence light below 650 nm;
focusing the refined fluorescence light below 650 nm onto a detector to generate a plurality of detection pulses;
generating a plurality of images of the oocytes comprising spatial information, spectral information and lifetime information;
assessing a metabolic activity of oocytes based on a plurality of fluorescence lifetimes of specific metabolites of the oocytes generated by fluorescence lifetime imaging microscopy (FLIM) using a principal component analysis phasor method on a FLIM microscopy apparatus, wherein fluorescence data from each pixel is transformed from a time domain to a frequency domain via Fourier transformation to produce phasor coordinates g and s, and wherein the phasor coordinates are populated into a phasor plot represented as a two-dimensional histogram, and wherein an analysis of the phasor plot calculates:
(a) a center of momentum defined by intensity-weighted average coordinates g and s across the unit cells of the histogram;
(b) an angle of a line joining an axis origin of the phasor plot and the center of momentum;
(c) two axes of a cluster in the phasor plot computed from eigenvalues and eigenvectors of the cluster distribution, giving a shape of a cluster cloud in terms of rotation and length; and
(d) a ratio of distances computed by determining phasor coordinates corresponding to an oxidative phosphorylation state and a glycolytic state based on known fluorescence lifetimes of protein-bound NADH and free NADH respectively, and calculating a position of the center of momentum relative to the oxidative and glycolytic state coordinates along a line connecting them in the phasor plot;
wherein the center of momentum, the angle, the two axes, and the ratio of distances are utilized as features to characterize each oocyte and are input to a plurality of machine learning algorithms for classification;
measuring oocyte media pH to assess the pH of the environment through a plurality of pH probes;
utilizing oocyte's morphological endpoints comprising shape and size from the spatial information; and
using the plurality of machine learning algorithms to integrate all sources of data and classify the oocytes for their viability based on a plurality of probability values.

2. The method according to claim 1 wherein assessing a metabolic activity of oocytes comprises measuring NADH, FAD and tryptophan concentrations in the oocytes; and measuring characteristic fluorescence lifetime fingerprint signatures.

3. The method according to claim 1 further comprising processing raw photon lifetime decay data to create a 2D heatmap, to reveal a plurality of patterns and variations in metabolic endpoints.

4. The method according to claim 1 further comprising generating a plurality of 2D and 3D plots to visualize the distribution of data across different Z-planes.

5. The method according to claim 1 further comprising classifying oocytes into aneuploids and euploids.

6. The method according to claim 1 wherein the imaging module device comprises a near IR diode laser, a beam expander, an excitation shutter, an emission shutter, a laser intensity control, a main dichroic, a focusing lens, a glavo scanning mirror, a photomultiplier, an emission filter, a constant fraction discriminator, a FLIM FPGA, a coupler, a graphical user interface and a QR activated petri-dish.

7. A system viability assessment in human oocytes, the system comprising:

an imaging module connected to a microscope that controls the light source and detection mechanism for the microscope, wherein the imaging module device comprises a near IR diode laser, a beam expander, an excitation shutter, an emission shutter, a laser intensity control, a main dichroic, a focusing lens, a glavo scanning mirror, a photomultiplier, an emission filter, a constant fraction discriminator, a FLIM FPGA, a coupler, a graphical user interface and a QR activated petri-dish;

a processor; and a user interface display;

wherein the imaging module is configured to focus a pulsed near infrared laser having an excitation wavelength in a range from 680 nanometers (nm) to 1000 nm at the plurality of oocytes for 2 and 3 photon absorption to cause the plurality of oocytes to emit fluorescence light, wherein the fluorescence light is in the visible light range ranging from 350 nanometers (nm) to 600 nm;

wherein the imaging module is configured to separate the fluorescence light using a dichroic mirror to reflect fluorescence light below 650 nm;

wherein the imaging module is configured to route the reflected fluorescence light below 650 nm through a spectral detection window comprising a plurality of emission filters to generate a refined fluorescence light below 650 nm;

wherein the imaging module is configured to focus the refined fluorescence light below 650 nm onto a detector to generate a plurality of detection pulses;

wherein the imaging module is configured to generate a plurality of images of the oocytes comprising spatial information, spectral information and lifetime information;

wherein the processor is configured to assess a metabolic activity of oocytes based on a plurality of fluorescence lifetimes of specific metabolites of the oocytes generated by fluorescence lifetime imaging microscopy (FLIM) using a principal component analysis phasor method on a FLIM microscopy apparatus, wherein fluorescence data from each pixel is transformed from a time domain to a frequency domain via Fourier transformation to produce phasor coordinates g and s, and wherein the phasor coordinates are populated into a phasor plot represented as a two-dimensional histogram, and wherein an analysis of the phasor plot calculates:

(a) a center of momentum defined by intensity-weighted average coordinates g and s across the unit cells of the histogram;

(b) an angle of a line joining an axis origin of the phasor plot and the center of momentum;

(c) two axes of a cluster in the phasor plot computed from eigenvalues and eigenvectors of the cluster distribution, giving a shape of a cluster cloud in terms of rotation and length; and (d) a ratio of distances computed by determining phasor coordinates corresponding to an oxidative phosphorylation state and a glycolytic state based on known fluorescence lifetimes of protein-bound NADH and free NADH respectively, and calculating a position of the center of momentum relative to the oxidative and glycolytic state coordinates along a line connecting them in the phasor plot;

wherein the center of momentum, the angle, the two axes, and the ratio of distances are utilized as features to characterize each oocyte and are input to a plurality of machine learning algorithms for classification;

wherein the processor is configured to measure oocyte media pH to assess the pH of the environment through a plurality of pH probes;

wherein the processor is configured to utilize oocyte's morphological endpoints comprising shape and size from the spatial information;

wherein the processor is configured to use a plurality of machine learning algorithms to integrate all sources of data and classify the oocytes for their viability based on a plurality of probability values.

8. The system according to claim 7 wherein the processor is configured to measure NADH, FAD and tryptophan concentrations in the oocytes; and measuring characteristic fluorescence lifetime fingerprint signatures.

9. The system according to claim 7 wherein the processor is configured to process raw photon lifetime decay data to create a 2D heatmap, to reveal a plurality of patterns and variations in metabolic endpoints.

10. The system according to claim 7 wherein the processor is configured to generate a plurality of 2D and 3D plots to visualize the distribution of data across different Z-planes.

11. The system according to claim 7 wherein the processor is configured to classify oocytes into aneuploids and euploids.

* * * * *